United States Patent [19]
Lamond et al.

[11] Patent Number: 5,658,316
[45] Date of Patent: Aug. 19, 1997

[54] PORTABLE DEFIBRILLATOR WITH DISPOSABLE POWER PACK

[75] Inventors: Pierre R. Lamond, Atherton; Bruno Strul, Portola Valley, both of Calif.

[73] Assignee: Automatic Defibrillator, Inc., Atherton, Calif.

[21] Appl. No.: 497,738

[22] Filed: Jul. 3, 1995

[51] Int. Cl.$^6$ .................................................. A61N 1/39
[52] U.S. Cl. .......................... 607/5; 607/142; 128/710
[58] Field of Search ............................ 607/5–8, 142; 128/696, 710–712; 307/150

[56] References Cited

U.S. PATENT DOCUMENTS

| | | |
|---|---|---|
| 4,023,573 | 5/1977 | Pantridge et al. |
| 4,510,935 | 4/1985 | Spencer ................................. 607/5 |
| 4,590,943 | 5/1986 | Paull et al. ............................ 607/5 |
| 4,610,254 | 9/1986 | Morgan et al. |
| 4,850,356 | 7/1989 | Heath ..................................... 607/5 |
| 4,981,141 | 1/1991 | Segalowitz ........................ 128/696 |
| 5,224,870 | 7/1993 | Weaver et al. ....................... 607/5 |
| 5,470,343 | 11/1995 | Fincke et al. ......................... 607/5 |

OTHER PUBLICATIONS

ANSI/AAMI, "Automatic External Defibrillators and Remote–Control Defibrillators", DF39, Sep. 16, 1993.

*Primary Examiner*—Jeffrey R. Jastrzab
*Attorney, Agent, or Firm*—Wilson Sonsini Goodrich & Rosati

[57] ABSTRACT

A portable defibrillator device has a housing including a disposable power pack and a main electronic unit. Treatment, ground pad and ECG electrodes are also included. One or more non-rechargeable batteries are positioned in the power pack, with each battery including battery contacts. An ECG detection circuit provides a control signal representative of heart activity. A defibrillation circuit is responsive to the control signal and is connected to the treatment electrode to deliver a discharge to the patient. In another embodiment, the portable defibrillator's housing includes a removable power pack and a main electronic unit. Disposed within the power pack are one or more batteries. A treatment electrode is capable of delivering a defibrillation shock and also measure ECG activity of a patient. A ground pad electrode is also included. An ECG detection circuit provides the control circuit, and a defibrillation circuit receives the control signal and delivers a treatment shock when appropriate. The defibrillation circuit is substantially positioned in the main electronic unit.

42 Claims, 5 Drawing Sheets

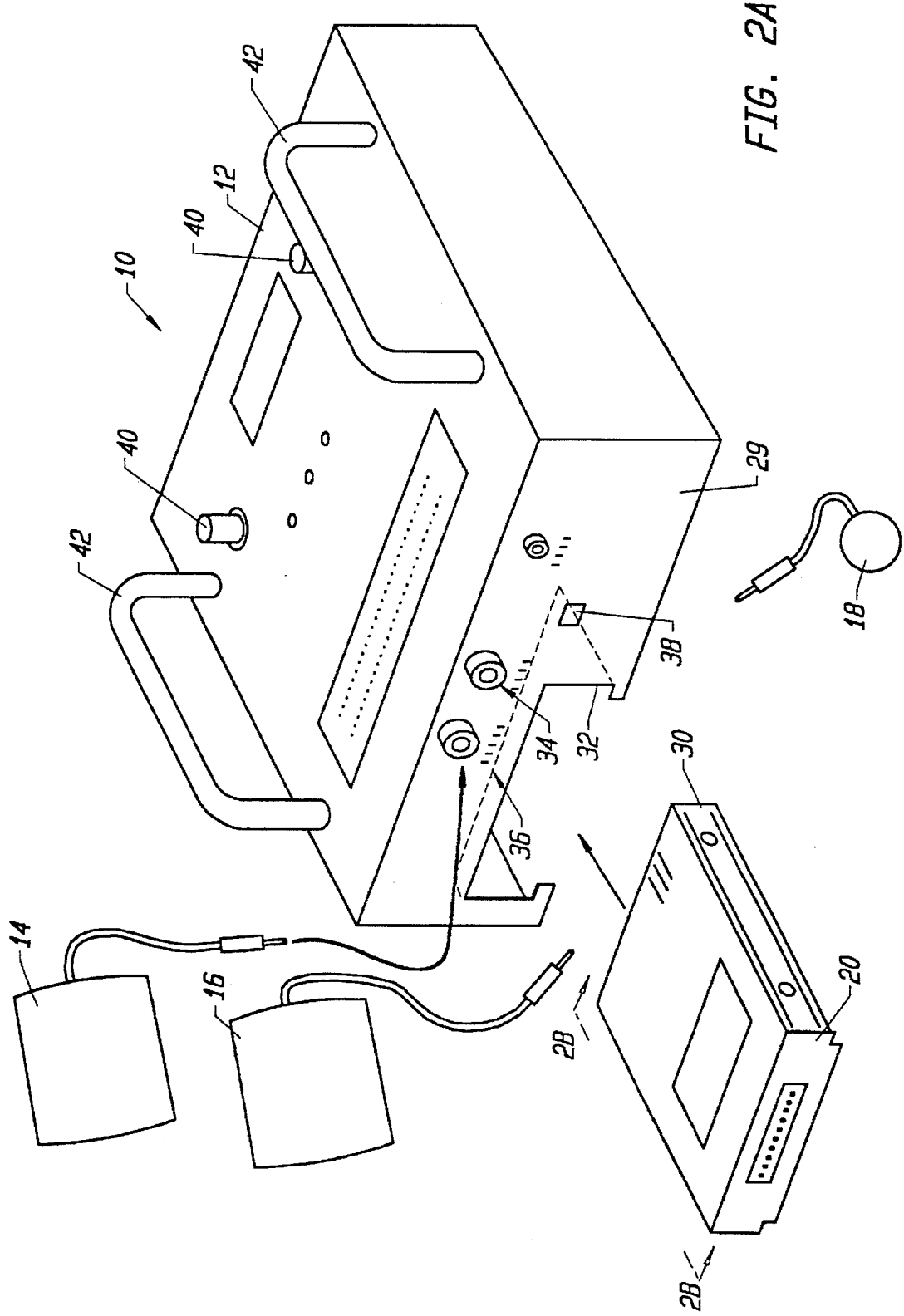

PORTABLE DEFIBRILLATOR WITH DISPOSABLE POWER PACK

BACKGROUND OF THE INVENTION

1. Field of the Invention

This invention relates to portable defibrillator devices, and more particularly, to a portable defibrillator device that has a disposable power pack which includes non-rechargeable batteries and a memory chip.

2. Description of Related Art

One of the most common and life threatening consequences of a heart attack is the development of a cardiac arrhythmia in which the heart is unable to pump a significant volume of blood. Unless a normal heart rhythm can be restored within a few minutes serious brain damage and death may result.

The most effective way to treat ventricular fibrillation is the application of an electric shock to the victim. The shock frequently terminates the chaotic activity of the arrhythmia and restores the normal pumping action of the heart. Defibrillators for producing and delivering such shocks have been known for many years. These defibrillators are usually large and relatively expensive. More recently, portable defibrillators have been introduced. However, even with the introduction of portable defibrillators, only a small percent of all ambulances are equipped with defibrillators.

Portable defibrillator devices currently available typically include rechargeable batteries. To keep them fully charged rechargeable batteries require constant maintenance. This adds to the expense of the portable defibrillator, and there are instances when the batteries are too low to deliver a defibrillation shock to the patient. Thus, there are safety concerns with the use of rechargeable batteries.

In other portable defibrillation devices an enable switch activates the battery pack. If one has forgotten to turn the apparatus off then the batteries are drained. Further there is no fail-safe mechanism in the event that the switch has been left on.

It is be desirable to provide a low cost portable defibrillator device which can be used in ambulances and in the home. It would also be desirable to provide a defibrillator device that has a disposable energy pack. Further, it would be desirable to provide a portable defibrillator device which includes low-cost components in a disposable energy pack, including non-rechargeable batteries and a memory chip. It would also be desirable to be provide a portable defibrillator device with a disposable energy pack that is activated when insulator strips, disposed between the non-rechargeable batteries and battery leads, are removed. It would also be desirable to include one or more memory chips in a power pack with the batteries in order to reduce loss of archival information.

SUMMARY OF THE INVENTION

Accordingly, it is an object of the invention to provide a low cost, portable defibrillator device.

Another object of the invention is to provide a safe, easy to operate, low, cost portable defibrillator device.

Still a further object of the invention it to provide a low cost, portable defibrillator device with a disposable energy pack.

Another object of the invention is to provide a low cost, portable defibrillator device with non-rechargeable batteries.

A further object of the invention is to provide a low cost, portable defibrillator device with a disposable energy pack that contains non-rechargeable batteries and a memory chip.

Yet another object of the invention is to provide a low cost, portable defibrillator device includes insulation sleeves positioned between the non-rechargeable batteries and battery leads.

A further object of the invention is to provide a low cost, portable defibrillator device that becomes activated when an insulator sleeve positioned between battery leads and the non-rechargeable batteries is removed.

Another object of the invention is to provide a low cost, portable defibrillator device that does not require active interaction between the defibrillator and the operator.

These and other objects of the invention are achieved in a portable defibrillator device that has a housing. The housing includes a disposable and removable power pack and a main electronic unit. Treatment, ground pad and ECG electrodes are used to detect and then deliver a shock to the heart if appropriate. One or more non-rechargeable batteries are positioned in the power pack. Each battery includes battery contacts. An ECG detection circuit provides a control signal that is representative of heart activity. A defibrillation circuit responds to the control signal, and is connected to deliver a discharge to the treatment electrode.

In another embodiment, the portable defibrillator device includes a housing with a removable power pack and a main electronic unit. The power pack includes one or more batteries. A treatment electrode is used that is capable of delivering a defibrillation shock and also measures ECG activity of a patient. Also included is a ground pad electrode. An ECG detection circuit provides a control signal that is representative of heart activity. A defibrillation circuit is responsive to the control signal and connected to deliver a discharge to the treatment electrode. The defibrillation circuit is substantially positioned in the main electronic unit.

One or more memory chips can be included in the power pack, and the batteries can be permanently fixed in the power pack. The main electronic unit includes a receiving slot with battery contacts that is adapted to make electrical contact with the batteries in the power pack. Removable insulators are positioned between the battery contacts of the receiving slot and the batteries. The batteries are electrically connected to the defibrillation circuit when the removable insulator is removed. Preferably, the batteries are non-rechargeable.

The portable defibrillator can also include a battery monitoring circuit. The battery monitoring circuit is continuously connected to the batteries when the power pack is positioned in the receiving slot of the main electronic unit.

A microprocessor is included in the defibrillation circuit. The ECG circuit includes signal conditioning and amplification circuits. The signal conditioner includes one or more filters and one or more amplifiers. The defibrillation circuit is made of a high voltage generator, an energy storage capacitor and a discharge switch. Further, the treatment and ground pad electrodes can be provided with electro-conductive gels.

BRIEF DESCRIPTION OF THE FIGURES

FIG. 2(a) is a perspective view of the portable defibrillator device of FIG. 1 with the power pack removed from the main housing.

DETAILED DESCRIPTION

Figure 1:
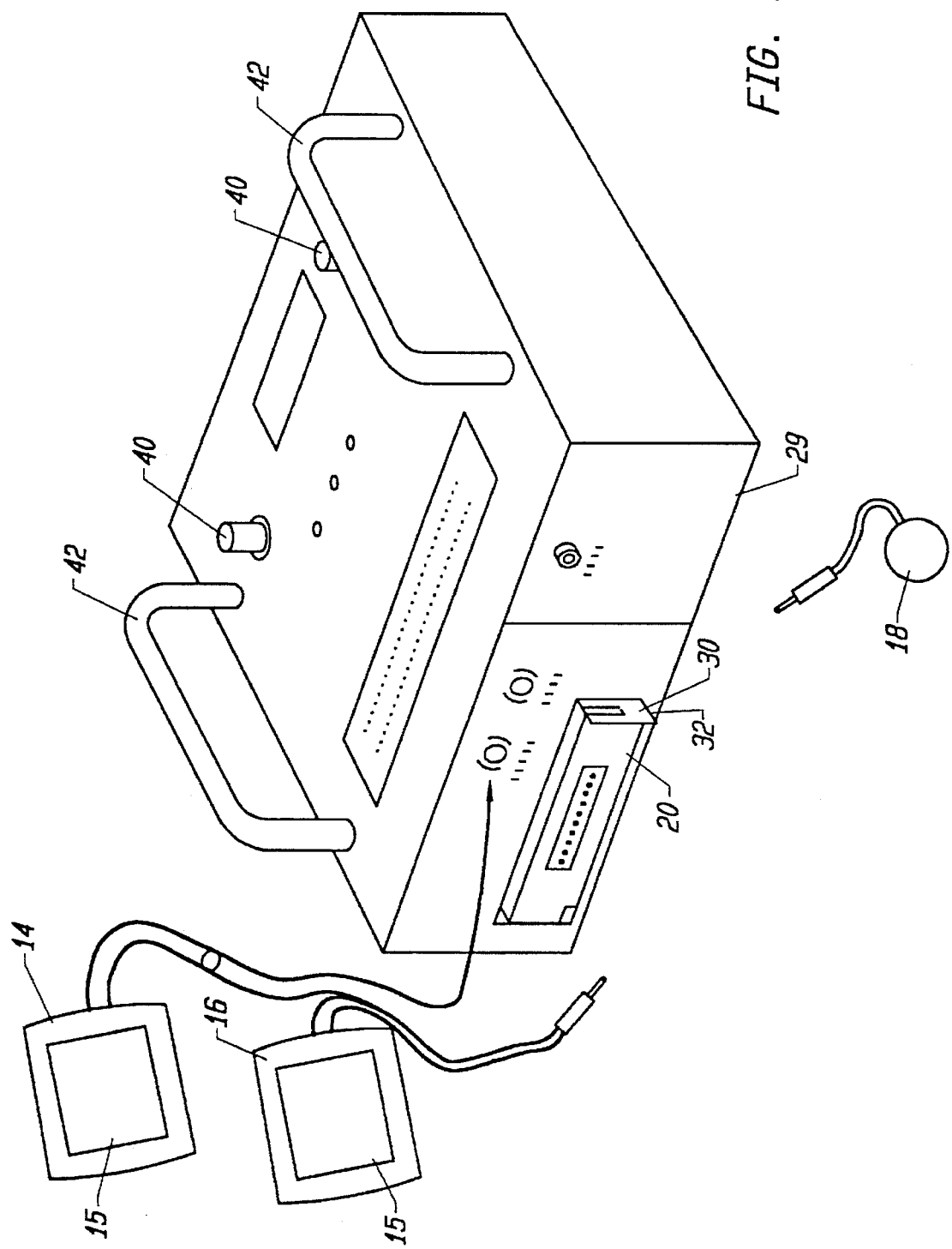
FIG. 1 is a perspective view of the portable defibrillator device of the present invention.
Figure 2B:
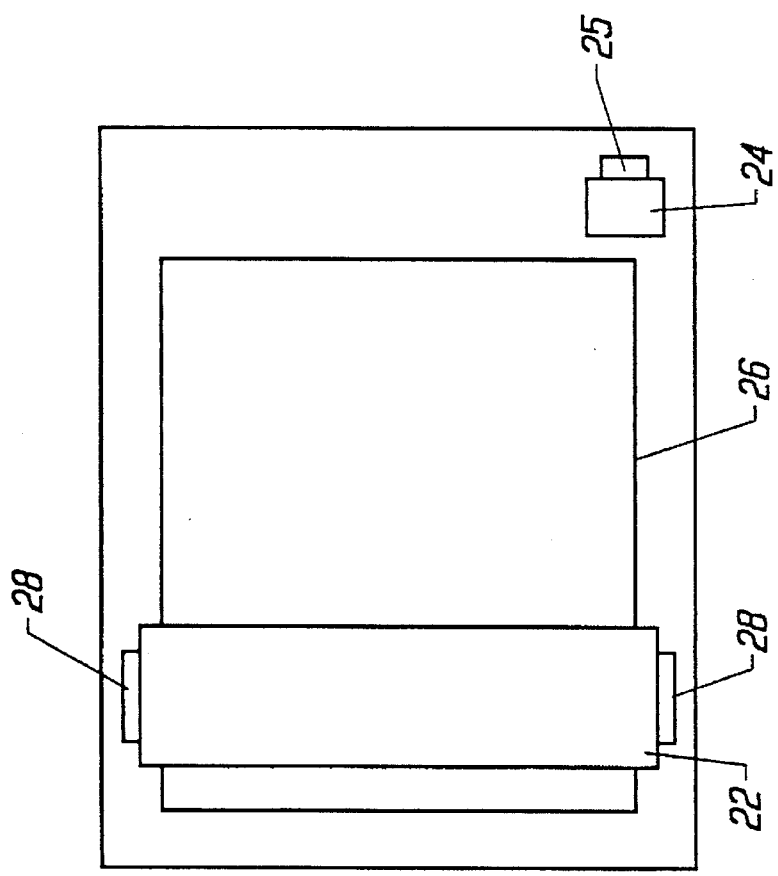
FIG. 2(b) is a cross-sectional view of the power pack illustrated in FIG. 2(a) taken along the lines 2(b)—2(b).

Referring now to FIGS. 1, 2(a) and 2(b), a portable defibrillator 10 includes a main housing 12 formed of a variety of materials well known to those skilled in the art. All of the components of portable defibrillator 10, including electronics and power pack, can be included in housing 12. A treatment electrode 14, ground pad electrode 16 and ECG 18 electrode are all coupled to housing 12. In some instances, only ground pad electrode 16 and treatment electrode 14 are required, and the function of ECG electrode 18 is included in treatment electrode 14.

Treatment electrode 14 delivers the shock to the heart and can be made an integral part of housing 12 or of the power pack, and is adapted to be placed on a patient's chest to deliver a defibrillation shock to a patient when appropriate. Treatment electrode 14 is made of materials, and is of similar size, of other defibrillator electrodes used with commercially available defibrillators. Treatment electrode 14 can also include a conductive gel 15. The gel 15 can be released through treatment electrode 14, on its exterior surface or applied to the patient's chest.

Ground pad electrode 16 and ECG electrode 18 are also placed on the patient. Preferably, ECG electrode 18 is placed near treatment electrode 14, and ground pad electrode 16 is positioned at another position on the patient's chest. Each of electrodes 14, 16 and 18 can connected with plugs to corresponding ports positioned on an exterior surface of housing 12. All three electrodes 14, 16 and 18 can be coated with an electro-conductive gel 15.

A power pack 20 is removable from housing 12. Included in power pack 20 is one or more non-rechargeable batteries, one or more memory chips 24, for built-in archival storage, memory chip contacts 25, a PC board 26 and battery contacts 28. Devices other than memory chips 24 can be utilized so long as they are capable of storing digitized ECG signals before and after application of the shock to the heart. Power pack 20 is disposable. The remaining electronics remain in a main electronic unit 29 included in housing 12, or alternatively in a separate module that can be part of housing 12. Power pack 20 and electrode 16 or 18 can be in one integral unit.

An instruction chart can be included on a top or side surface of main housing 12, as well as LED's and an electro-mechanical indicator advising if a shock has been sent to the patient. Further labeling can be applied to the outside of power pack 20.

Power pack 20, with or without one or more electrodes 14, 16 or 18, is sealed in standard insulating packaging material, such as electrical insulator 30. Electrical insulator 30 can be the backing for electrodes 14, 16 or 18. Power pack 20 is positioned in a receiving slot 32, defined by main housing 12. Electrical insulator 30 is positioned between battery contacts 28 and battery contacts 34 and 36. When positioned between opposing battery contacts, electrical insulator 30 precludes the completion of a circuit, and thus permits the practical use of non-rechargeable batteries.

When electrical insulator 30 is removed, electrodes 14, 16 and 18 are ready for attachment, and the batteries are then electrically connected to main electronic unit 29. Power pack 20 is guaranteed for single use until its expiration date. For purposes of this disclosure, single use is defined as an ability to deliver the minimum number of shocks at the prescribed level by AAMI guidelines. AAMI standard, Association for the Advancement of Medical Instrumentation, "*Automatic external defibrillators and remote-control defibrillators*", ANSI/AAMI DF39-1993, this document is herein incorporated by reference. Power pack 20 may not be salvageable once electrical insulator 30 is removed. At this point, it is then necessary to replace power pack 20.

A monitoring circuit periodically monitors the functionality of main electronic unit 29. If main electronic unit fails any test than monitoring circuit sends a visual or audible warning signal.

Treatment electrode 14 is positioned on an exterior surface of power pack 20. Before defibrillator device 10 is used on a patient electrical insulator is removed. This rest fits in a completion of the defibrillation circuit and treatment can begin, as more fully explained hereafter. After defibrillation device 10 is used on a patient, and a shock has been successfully delivered, power pack 20 is removed from receiving slot 32 and returned for replacement. The used power pack 20 contains archival data on its internal memory chip that needs to be read by a special reader to produce a chart of the patient's cardiac electrical activity before and after the treatment.

In one embodiment, the requirements for a one-use portable defibrillator 10 is to deliver six (6) pulses of electricity, 360 joules each, thirty seconds apart. Altogether there are 2,160 joules. With eight D-size alkaline batteries, there are 12 volts with 2 amps/hour capacity which provide 86,400 joules.

ECG electrode 18 produces a control signal to a defibrillation circuit 38. Batteries 22 in power pack 20 are connected to a high voltage generation circuit when electrical insulator 30 is removed, in order to deliver a discharge. Treatment electrode 14 then provides a defibrillation shock in response to receipt of a control signal from a microprocessor.

When an operator decides to use defibrillator device 10 it is first used in a diagnostic mode. Defibrillator device 10 determines if the patient is in need of a shock. If so, then the operator pulls electrical insulator 30 to remove it. This action connects power pack 20, specifically non-rechargeable batteries 22, to defibrillation circuit 38, and defibrillation circuit 38 is activated. Non-rechargeable batteries 22 can be permanently installed in power package 20 and soldered into PC board 26. One or two enable switches 40 can be included in one or both of handles 42. ECG electrode 18 is placed into contact on the patient's chest to determine ECG activity. Ground pad electrode 16 is removed from housing 12, or power pack housing 20, and placed on the chest or on a side of the patient. It will be appreciated that the functions of electrodes 14 and 16 can be included in a single treatment/ECG electrode.

The operator then holds housing 12 with handles 42, making sure there is good contact between treatment electrode 14 and the patient's chest at a location where the heart is. Although FIGS. 1 and 2 show that two handles are included, it is possible that only one is necessary, or alternatively, the operator can apply sufficient pressure to make the intimate contact between treatment electrode 14 and the patient's chest. In any event, it is important that the operator not receive a shock when the defibrillation shock is delivered from treatment electrode 14 to the patient. For this reason, it is desirable to include two handles 42 so that the operator does not have the occasion to have one hand touching the patient when the defibrillation shock is delivered to the patient.

Further one or more enable switches 40 are included and positioned adjacent to handles 42 or are directly on handles 42. Enable switches 40 provide the operator with an ability to stop the procedure for a variety of reasons, including but not limited to, (i) someone is touching the patient, (ii) the operator is touching the patient, or (iii) the patient begins to move, as well as many other instances where it is desirable for the operator to be able to stop the defibrillation process.

A display can be included but is not necessary. A variety of different messages can be seen with a display. If a display is provided it can be spring loaded and activated with a solenoid. The operator does not have to provide feedback information to portable defibrillation device 10. Thus, all the operator needs to do is to remove electrical insulator 30, apply electrode 14 to the patient's chest, apply electrode 16 to the patient's chest, and then if it is appropriate, defibrillation device 10 applies the necessary defibrillation shocks if the operator activates enable switches 40. The safety of the operator is insured with the inclusion of handles 42.

Portable defibrillator 10 can also include a monitoring circuit which is continuously connected to main electronic unit 29.

Figure 3:
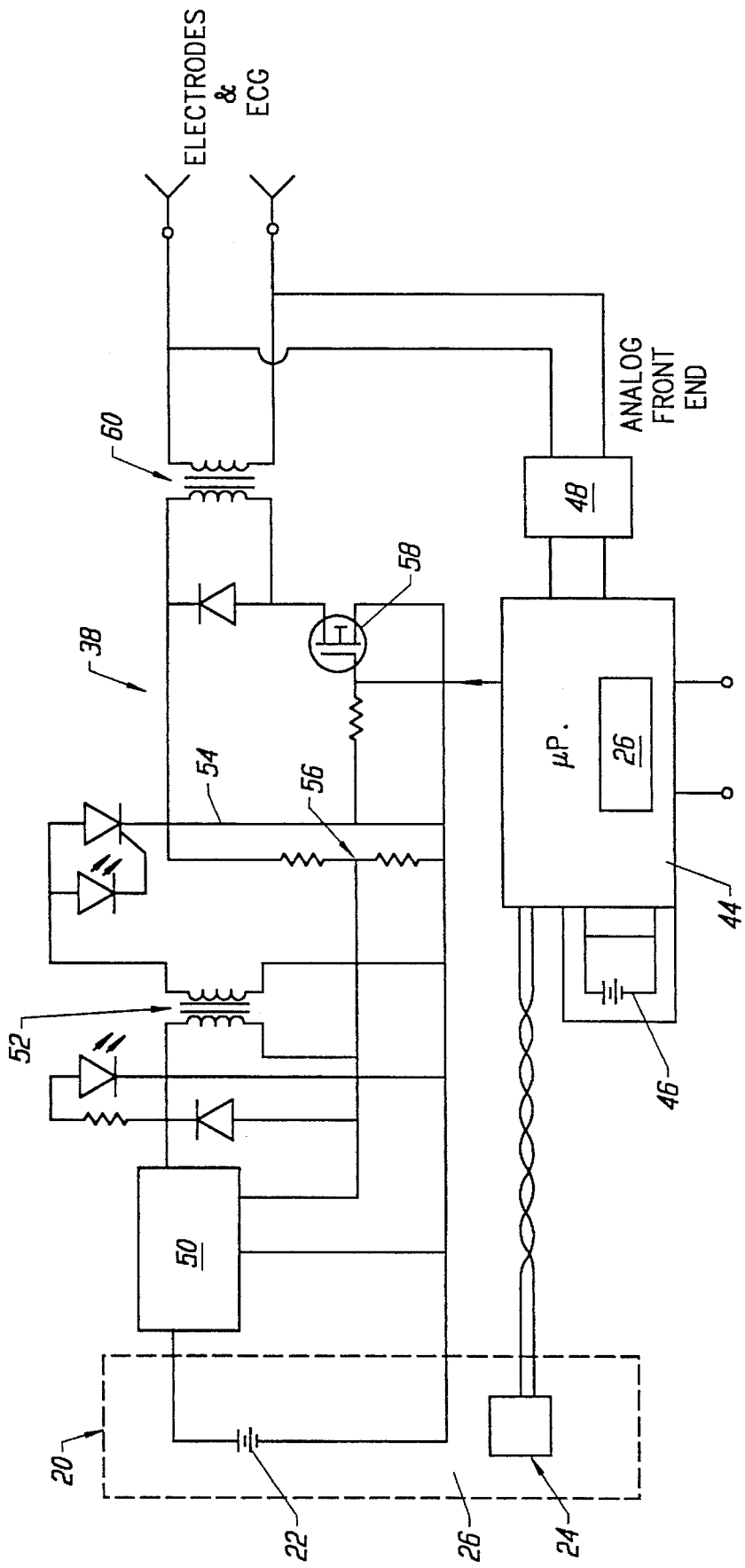
FIG. 3 is a schematic diagram of one embodiment of the electronics of the present invention.

Referring to FIG. 3, memory chip 24 communicates with one or more wires to main electronic unit 29. Included in main electronic unit 29 is a microprocessor 44 such as a model no. 68HC11, available from Motorola. Coupled to microprocessor 44 is a battery 46 for main electronic unit 29, and an analog front end 48 which can include one or more filters, an isolation apparatus and amplifiers, that are used for monitoring purposes for ECG electrode 18.

After electrodes 14, 16 and 18 are in place, an ECG signal is analyzed at microprocessor 44. If the patient is shockable a visual and/or audio signal is sent. The visual signal can emanate from a light or an LED.

Figure 4:
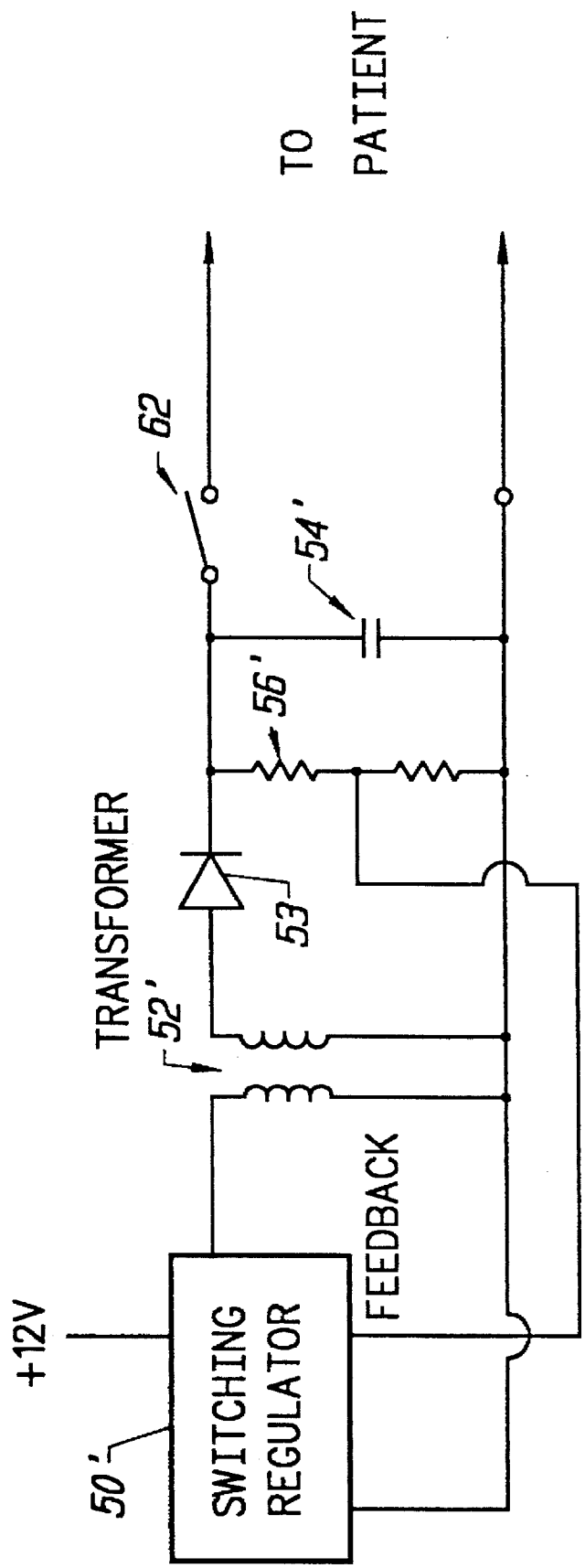
FIG. 4 is a schematic diagram of a second embodiment of the electronics of the present invention.

Two different embodiments of the electronics of the invention are disclosed in FIGS. 3 and 4. A switching regulator 50, 50' is connected to microprocessor 44 and to a transformer 52,52'. An output of transformer 52 is about 100 to 500 volts, and the output of 52' is about 1000 to 5000 volts. Transformers 52 and 52' transmit energy to storage capacitor 54, 54' which then creates the discharge for the shock that is delivered to the patient via electrode 14. It requires about 15 seconds to charge up capacitor 54, 54'. A voltage divider 56, 56' across capacitor 54, 54' creates a controlled feedback system where capacitor 54, 54' is charged for a voltage corresponding to a known energy level according to the formula $E=CV^2/2$. Capacitor 54, 54' is charged to a known energy. When it is time to shock the patient a signal is sent from microprocessor 44 to a semiconductor switch 58 or switch 62. Capacitor 54, 54' then discharges through transformer 60 in FIG. 3 or directly to electrode 14 in FIG. 4. An alternative circuit charges capacitor 54' to 1000 to 5000 volts. A high voltage switch discharges to the patient.

An algorithm is associated with microprocessor 44 which digitizes the signal received from ECG electrode 18. The ECG signal is digitized and analyzed. Energy builds up in capacitor 54, 54'. If it is determined by the analysis of ECG signal that a shock is required, then capacitor 54 discharges energy through transformer 60 to electrode 14 or from capacitor 54' directly to electrode 14. This can be repeated up to five or six times. Further, capacitor 54, 54' can be recharged to different levels by changing the voltage. This is achieved by including different tabs, coupled to voltage divider 56, 56' with controls on a front panel of housing 12.

In the embodiment of FIG. 4, capacitor 54' does not discharge to a transformer. A diode 53 prevents capacitor 54' from discharging to transformer 52'.

Further details regarding the electronics and suitable software are found in U.S. Pat. No. 4,610,254, incorporated herein by reference.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A portable defibrillator device, comprising:

a housing including a disposable power pack and a main electronic unit with an ECG detection circuit that provides a control signal representative of heart activity, wherein the power pack includes an insulator member configured to be removed from the power pack to provide a coupling of the power pack to the main electronic unit;

a treatment electrode coupled to the power pack and the main electronic unit;

a ground pad electrode coupled to the power pack and the main electronic unit;

an ECG electrode coupled to the ECG detection circuit;

one or more non-rechargeable batteries positioned in the power pack, each battery including battery contacts; and a defibrillation circuit responsive to the control signal and configured to deliver a discharge to the treatment electrode, wherein the defibrillation circuit is included as at least a part of the main electronic unit.

2. The portable defibrillator of claim 1, further comprising:

a removable insulator positioned between battery contacts and the main electronic unit, wherein the non-rechargeable batteries are electrically connected to the defibrillation circuit when the removable insulator is removed.

3. The portable defibrillator of claim 1, wherein the functionality of the treatment electrode and the ECG electrode are included in a single electrode.

4. The portable defibrillator of claim 1, wherein the housing includes a receiving slot with battery contacts.

5. The portable defibrillator of claim 4, wherein the power pack is removably positioned in the receiving slot.

6. The portable defibrillator of claim 1, further comprising:

a battery monitoring circuit coupled to the main electronic unit.

7. The portable defibrillator of claim 6, wherein the battery monitoring circuit is continuously connected to the non-rechargeable batteries when the power pack is positioned adjacent to the main electronic unit.

8. The portable defibrillator of claim 6, wherein the battery monitoring circuit periodically checks a status of the non-rechargeable batteries.

9. The portable defibrillator device of claim 1, further comprising:

a microprocessor coupled to the defibrillation circuit.

10. The portable defibrillator device of claim 1, wherein the ECG circuit includes a signal conditioner and an amplifier.

11. The portable defibrillator device of claim 10, wherein the signal conditioner includes one or more filters and one or more amplifiers.

12. The portable defibrillator device of claim 1, wherein the defibrillation circuit includes a high voltage generator, an energy storage capacitor and a discharge switch.

13. The portable defibrillator device of claim 1, wherein the non-rechargeable batteries are continuously connected to the battery monitoring circuit when the power pack is positioned in the housing, and the power pack is coupled to the defibrillation circuit when the insulator member is removed and the power pack is positioned in the housing.

14. The portable defibrillator of claim 1, further comprising:
an operator support that permits an operator of the portable defibrillator device to physically apply the treatment electrode when the treatment electrode is positioned on at least a portion of an exterior surface of the power pack to a patient and create a contact between the patient and the treatment electrode without subjecting the operator to a shock when the treatment electrode delivers a shock to the patient.

15. The portable defibrillator of claim 14, wherein the operator support includes at least one handle attached to the housing.

16. The portable defibrillator of claim 14, wherein the operator support includes at least two handles attached to the housing.

17. The portable defibrillator of claim 1, wherein the treatment electrode includes an electro-conductive gel.

18. The portable defibrillator of claim 1, wherein the ground pad electrode has an electrode surface that includes an electro-conductive gel.

19. The portable defibrillator of claim 1, wherein the ECG detection circuit receives ECG signals from the ECG electrode and processes the ECG signals and wherein the power pack includes a memory chip for storing the processed ECG signals.

20. A portable defibrillator device, comprising:
a housing including a removable power pack including one or more non-rechargeable batteries and a main electronic unit including an ECG detection circuit providing a control signal representative of heart activity, wherein the power pack includes an insulator member configured to be removed from the power pack to provide a coupling of the power pack to the main electronic unit;
a treatment electrode configured to deliver a defibrillation shock and measure ECG activity of a patient, wherein the treatment electrode is coupled to the power pack and the main electronic unit;
a ground pad electrode coupled to the power pack and the main electronic unit;
a defibrillation circuit responsive to the control signal and configured to deliver a discharge to the treatment electrode, wherein at least a portion of the defibrillation circuit is included in the main electronic unit.

21. The portable defibrillator of claim 20, wherein the ECG detection circuit receives ECG signals from the treatment electrode and processes the ECG signals and wherein the power pack includes a memory chip for storing the processed ECG signals.

22. The portable defibrillator of claim 20, wherein the housing includes a receiving slot with battery contacts adapted to make electrical contact with the batteries in the power pack.

23. The portable defibrillator of claim 20, further comprising: a battery monitoring circuit coupled to the main electronic unit.

24. The portable defibrillator of claim 23, wherein the battery monitoring circuit is continuously connected to the batteries when the power pack is positioned adjacent to the main electronic unit.

25. The portable defibrillator device of claim 20, further comprising:
a microprocessor included in the defibrillation circuit.

26. The portable defibrillator device of claim 20, wherein the ECG circuit includes a signal conditioner and an amplifier.

27. The portable defibrillator device of claim 26, wherein the signal conditioner includes one or more filters and one or more amplifiers.

28. The portable defibrillator device of claim 28, wherein the defibrillation circuit includes a high voltage generator, an energy storage capacitor and a discharge switch.

29. The portable defibrillator of claim 20, further comprising:
an operator support that permits an operator of the portable defibrillator device to physically apply the treatment electrode when the treatment electrode is positioned on at least a portion of an exterior surface of the power pack to a patient and create a contact between the patient and the treatment electrode without subjecting the operator to a shock when the treatment electrode delivers a shock to the patient.

30. The portable defibrillator of claim 29, wherein the operator support includes at least one handle attached to the housing.

31. The portable defibrillator of claim 29, wherein the use support includes at least two handles attached to the housing.

32. The portable defibrillator of claim 29, further comprising:
a defibrillation circuit enable switch positioned at one of a handles, wherein upon closing of the enable switch the defibrillation circuit is coupled to the main electronic unit.

33. The portable defibrillator of claim 20, wherein the treatment electrode includes an electro-conductive gel.

34. The portable defibrillator of claim 20, wherein the ground pad electrode has an electrode surface that includes an electro-conductive gel.

35. A potable defibrillator device, comprising:
a housing including a power pack;
a treatment electrode coupled to the power pack;
a ground pad electrode coupled to the power pack;
an ECG electrode for generating ECG signals coupled to the power pack;
one or more bakeries positioned in the power pack each battery including battery contacts;
an ECG detection circuit for receiving the ECG signals from the ECG electode processing the ECG signals providing a control signal representative of heart activity;
a defibrillation circuit responsive to the control signal and configured to deliver a discharge to the treatment electrode; and
a memory device configured to store the processed ECG signals before and after application of a defibrillation shock, wherein the memory device is positioned in the power pack.

36. The portable defibrillator device of claim 35, wherein the memory device is one or more memory chips.

37. A portable defibrillator device, comprising:
a housing including a power pack;

a treatment electrode coupled to the power pack;

a ground pad electrode coupled to the power pack;

an ECG electrode coupled to the power pack;

an insulator packaging the power pack one or more of the electrodes the insulator being at least partially removable from the power pack;

one or more batteries positioned in the power pack, each of the one or more batteries including battery contacts;

an ECG detection circuit for receiving the ECG signals from the ECG electrode, processing the ECG signals and providing a control signal representative of heart activity, wherein the ECG detection circuit is coupled to the power pack; and a defibrillation circuit coupled to the treatment electrode and the ground pad electrode and responsive to the control signal and configured to deliver a discharge to the treatment electrode, wherein the defibrillation circuit is coupled to the power pack.

38. The portable defibrillator device of claim 37, comprising:

a memory device to store the processed ECG signals before and after application of a defibrillation shock, wherein the memory device is positioned in the power pack.

39. The portable defibrillator device of claim 38, wherein the memory device is one or more memory chips.

40. A portable defibrillator device, comprising:

a housing including a power pack;

a treatment electrode configured to deliver a defibrillation shock and measure ECG activity of a patient, wherein the treatment electrode is coupled to the power pack;

a ground pad electrode coupled to the power pack;

one or more batteries positioned in the power pack, each battery including battery contacts;

an ECG detection circuit for receiving the ECG signals from the ECG electrode processing the ECG signals and providing a control signal representative of heart activity;

a defibrillation circuit responsive to the control signal and configured to deliver a discharge to the treatment electrode; and a memory device configured to store the processed ECG signals before and after application of a defibrillation shock, wherein the memory device is positioned in the power pack.

41. A portable defibrillator device, comprising:

a housing including a power pack;

a treatment electrode configured to deliver a defibrillation shock and measure ECG activity of a patient, wherein the treatment electrode is coupled to the power pack;

a ground pad electrode coupled to the power pack;

an insulator packaging the power pack with one or more of the electrodes the insulation being at least partially removable from the power pack;

one or more batteries positioned in the power pack, each battery including battery contacts;

an ECG detection circuit configured to supply a control signal representative of heart activity, wherein the ECG detection circuit is coupled to the power pack; and a defibrillation circuit coupled to the treatment electrode and the ground pad electrode responsive to the control signal and configured to deliver a discharge to the treatment electrode, wherein the defibrillation circuit is coupled to the power pack.

42. A portable defibrillator device, comprising:

a housing including a removable power pack including one or more non-rechargeable batteries and a main electronic unit including an ECG detection circuit providing a control signal representative of heart activity, wherein the power pack includes an insulator member configured to be at least partially removed from the power pack to provide a coupling of the power pack to the main electronic unit;

a treatment electrode configured to deliver a defibrillation shock to a patient and coupled to the power pack and the main electronic unit; and a ground pad electrode coupled to the power pack and the main electronic unit;

a defibrillation circuit, coupled to the ground pad electrode and the treatment electrode and responsive to the control signal, configured to deliver a discharge to the treatment electrode, wherein at least a portion of the defibrillation circuit is included in the main electronic unit.

* * * * *